United States Patent
Umehara (10) Patent No.: US 10,261,024 B2
(45) Date of Patent: Apr. 16, 2019

(54) VISUAL INSPECTION DEVICE AND VISUAL INSPECTION METHOD

(71) Applicant: JTEKT CORPORATION, Osaka-shi, Osaka (JP)

(72) Inventor: Jiro Umehara, Toyonaka (JP)

(73) Assignee: JTEKT CORPORATION, Osaka (JP)

( * ) Notice: Subject to any disclaimer, the term of this patent is extended or adjusted under 35 U.S.C. 154(b) by 0 days.

(21) Appl. No.: 15/499,123

(22) Filed: Apr. 27, 2017

(65) Prior Publication Data

US 2017/0328838 A1    Nov. 16, 2017

(30) Foreign Application Priority Data

May 13, 2016 (JP) ................................. 2016-096806

(51) Int. Cl.
*G01N 21/00* (2006.01)
*G01N 21/88* (2006.01)

(52) U.S. Cl.
CPC ..... *G01N 21/8803* (2013.01); *G01N 21/8806* (2013.01); *G01N 2021/8812* (2013.01)

(58) Field of Classification Search
CPC ........................... G01N 21/8803; G01N 21/00
USPC ....................................................... 356/237.5
See application file for complete search history.

(56) References Cited

U.S. PATENT DOCUMENTS

| | | | | |
|---|---|---|---|---|
| 2,560,200 A * | 7/1951 | Werzyn | ................ | G03B 15/03 362/239 |
| 3,187,170 A * | 6/1965 | Kille | ................ | G03B 15/05 362/258 |
| 3,893,145 A * | 7/1975 | King | ................ | G03B 15/05 362/8 |
| 3,970,835 A * | 7/1976 | Crete | ................ | G03B 15/02 362/11 |
| 4,051,493 A * | 9/1977 | Nakagawa | ........... | G03B 15/041 362/3 |
| 4,078,170 A * | 3/1978 | Sloop | ................ | G03B 15/0442 359/847 |
| 4,081,814 A * | 3/1978 | Bulland | ................ | F16M 11/28 248/187.1 |
| 4,091,402 A * | 5/1978 | Siegel | ................ | G03B 15/041 362/3 |
| 4,241,988 A * | 12/1980 | Lepp | ................ | F16M 11/08 248/183.1 |

(Continued)

FOREIGN PATENT DOCUMENTS

| | | | | |
|---|---|---|---|---|
| JP | 2002-116153 A | | 4/2002 | |
| JP | 2013096967 A | * | 5/2013 | ........... G01N 21/954 |

OTHER PUBLICATIONS

Oct. 19, 2018 Office Action issued in U.S. Appl. No. 15/666,218.

*Primary Examiner* — Roy M Punnoose
(74) *Attorney, Agent, or Firm* — Oliff PLC (57) ABSTRACT

A visual inspection device is an inspection device using an image obtained by shooting an inspection surface of an object to be inspected with a camera disposed so as to face the inspection surface. The object to be inspected is a rolling bearing and the inspection surface is a surface included in an outer ring of the rolling bearing. A lighting device emits light from a light source as diffused light to the inspection surface in a direction different from a direction in which the camera shoots the inspection surface, and the camera shoots the inspection surface irradiated with the diffused light.

5 Claims, 6 Drawing Sheets

(56) References Cited

U.S. PATENT DOCUMENTS

| | | | | |
|---|---|---|---|---|
| 4,259,000 A | * | 3/1981 | Heredia | G03B 17/566 |
| | | | | 396/422 |
| 4,512,644 A | * | 4/1985 | Yoshida | G03B 15/05 |
| | | | | 396/174 |
| 4,710,005 A | * | 12/1987 | Bennett | G03B 15/05 |
| | | | | 362/3 |
| 4,752,794 A | * | 6/1988 | Bohannon | F16M 11/2028 |
| | | | | 362/11 |
| 5,194,885 A | * | 3/1993 | Spencer | G03B 15/05 |
| | | | | 396/182 |
| 5,275,364 A | * | 1/1994 | Burger | F16L 3/00 |
| | | | | 248/125.1 |
| 5,761,550 A | * | 6/1998 | Kancigor | G03B 15/05 |
| | | | | 362/8 |
| 6,042,277 A | * | 3/2000 | Errington | G03B 15/05 |
| | | | | 248/187.1 |
| 6,384,863 B1 | * | 5/2002 | Bronson | H04N 5/2251 |
| | | | | 348/208.99 |
| 7,957,636 B2 | * | 6/2011 | Saitoh | G01N 21/8806 |
| | | | | 396/155 |
| 8,736,710 B2 | * | 5/2014 | Spielberg | G03B 15/05 |
| | | | | 348/222.1 |
| 2001/0012393 A1 | * | 8/2001 | Yonezawa | G01N 21/8803 |
| | | | | 382/145 |
| 2004/0184031 A1 | * | 9/2004 | Vook | G06T 7/0002 |
| | | | | 356/237.1 |
| 2005/0025353 A1 | | 2/2005 | Kaneko et al. | |
| 2010/0118136 A1 | * | 5/2010 | Riet | G01B 11/306 |
| | | | | 348/92 |
| 2010/0296096 A1 | | 11/2010 | Horvath et al. | |

* cited by examiner

VISUAL INSPECTION DEVICE AND VISUAL INSPECTION METHOD

INCORPORATION BY REFERENCE

The disclosure of Japanese Patent Application No. 2016-096806 filed on May 13, 2016 including the specification, drawings and abstract, is incorporated herein by reference in its entirety.

BACKGROUND OF THE INVENTION

1. Field of the Invention

The present invention relates to visual inspection devices and visual inspection methods.

2. Description of the Related Art

An inspection method based on high surface reflectance, namely based on surface gloss, is known as one of visual inspection methods for industrial products such as rolling bearings. Specifically, as is also disclosed in Japanese Patent Application Publication No. 2002-116153 (JP 2002-116153 A), such a visual inspection method is commonly performed by analyzing a captured image of a surface. More specifically, this inspection method includes shooting an inspection surface of an object to be inspected while illuminating the inspection surface with a lighting device, and analyzing a captured image. Through the analysis, any irregularities such as flaws on the inspection surface are detected as defective gloss. Specifically, since light emitted from the lighting device is reflected in various directions by irregularities on the inspection surface, the amount of light reflected from the inspection surface into a camera varies between the region having irregularities and the region having no irregularities. The irregularities on the inspection surface can be detected by detecting the difference in the amount of light reflected from the inspection surface into the camera by shades in the captured image.

In such conventional visual inspection as disclosed in JP 2002-116153 A, a camera is disposed so as to face an inspection surface of an object to be inspected, and a half mirror is disposed between the camera and the inspection surface. Light from a light source is thus emitted to the inspection surface in the same direction as the direction in which the camera shoots the inspection surface. The inspection surface is thus most efficiently irradiated with light. In this case, however, the proportion of the amount of light reflected from the inspection surface into the camera to the amount of light emitted to the inspection surface is very high. The difference between the amount of light reflected from the region of the inspection surface having irregularities and the amount of light reflected from the region of the inspection surface having no irregularities is very small. Namely, the difference in shades in the captured image is small. This may reduce accuracy of detection of defects in appearance.

SUMMARY OF THE INVENTION

It is one object of the present invention to provide a visual inspection device that conducts visual inspection with high accuracy, and a visual inspection method.

A visual inspection device according to an aspect of the present invention includes: a camera that is disposed so as to face a first inspection surface of an object to be inspected and that shoots the first inspection surface; and a lighting device that emits light from a light source as diffused light to the first inspection surface in a direction different from a direction in which the camera shoots the first inspection surface.

BRIEF DESCRIPTION OF THE DRAWINGS

The foregoing and further features and advantages of the invention will become apparent from the following description of example embodiments with reference to the accompanying drawings, wherein like numerals are used to represent like elements and wherein.

DETAILED DESCRIPTION OF EMBODIMENTS

Preferred embodiments will be described below with reference to the accompanying drawings. In the following description, the same parts and components are denoted with the same reference characters. The names and functions of these parts and components are also the same. Accordingly, description thereof will not be repeated.

A visual inspection device 100 according to an embodiment of the present invention conducts visual inspection of an industrial product with a high reflectance surface, namely a glossy surface. For example, an object to be inspected by the visual inspection device 100 is a rolling bearing. In the following description, the visual inspection device 100 inspects an inspection surface included in the outer periphery of an outer ring of a rolling bearing. A rolling bearing 300, which is an object to be inspected by the visual inspection device 100, has an outer ring 300A, an inner ring 300B, a plurality of rolling elements 300C, a cage 300D, and a bearing seal 300E.

Figure 1:
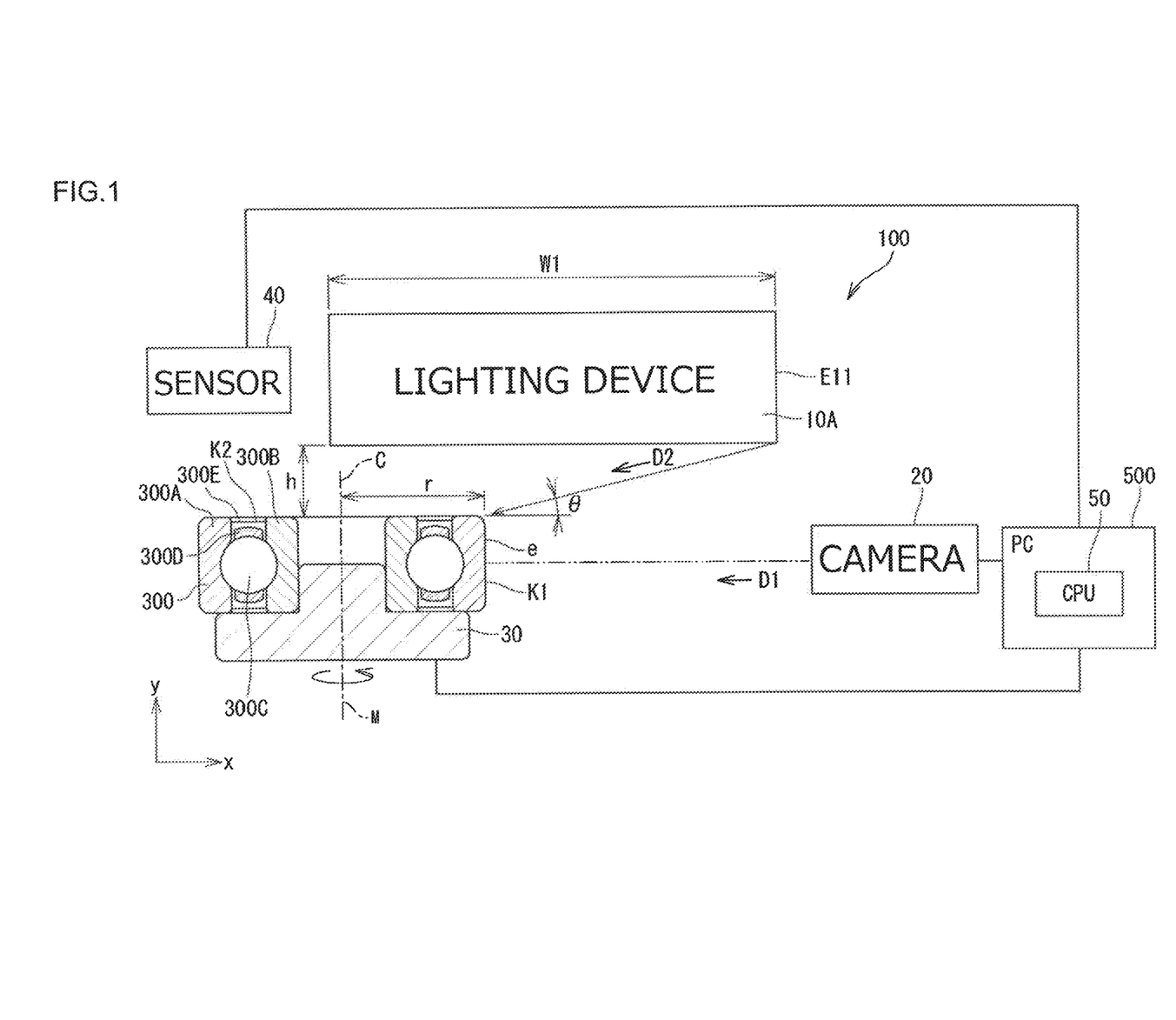
FIG. 1 is a schematic view of a visual inspection device according to an embodiment as viewed from the front.

FIG. 1 is a schematic view of the visual inspection device 100 according to the embodiment as viewed from the front. Referring to FIG. 1, the visual inspection device 100 includes a lighting device 10A, a camera 20, and a stand 30. The lighting device 10A emits light from a light source to a first inspection surface K1 of the rolling bearing 300. The first inspection surface K1 is a surface included in the outer periphery of the outer ring 300A of the rolling bearing 300 that is an object to be inspected. The camera 20 shoots the first inspection surface K1. The stand 30 has a horizontal mount surface, and the rolling bearing 300 is placed on this horizontal mount surface. Preferably, the visual inspection device 100 further includes a sensor 40. The sensor 40 is a displacement sensor. The visual inspection device 100 including the sensor 40 will be described later as a second embodiment. In the first embodiment, the visual inspection device 100 does not include the sensor 40.

The rolling bearing 300 is placed on the stand 30 such that the central axis C of the rolling bearing 300 extends in the vertical direction. The camera 20 is disposed so as to face the first inspection surface K1 included in the outer periphery of the outer ring 300A of the rolling bearing 300. Specifically, the camera 20 is disposed such that the direction D1 (shooting direction) in which the camera 20 shoots the first inspection surface K1 is perpendicular to the direction of the central axis C of the rolling bearing 300 placed on the stand 30. In the example of FIG. 1, since the direction of the central axis C is the vertical direction, the shooting direction D1 is one horizontal direction.

The camera 20 is connected to a computer (personal computer (PC)) 500 serving as a control device and sends a captured image to the PC 500. The PC 500 includes a central processing unit (CPU) 50 that controls the PC 500.

In the following description, as shown in FIG. 1, the x direction is the direction parallel to the shooting direction D1. In the example of FIG. 1, the x direction is the horizontal direction. The shooting direction D1 is the negative x direction (also referred to as the "−x direction"), and the opposite direction of the shooting direction D1 is the positive x direction (also referred to as the "+x direction"). The y direction is the direction of the central axis C. In the example of FIG. 1, the y direction is the vertical direction. The direction toward the lighting device 10A in the direction of the central axis C is the positive y direction (also referred to as the "+y direction"), and the opposite direction of this direction is the negative y direction (also referred to as the "−y direction").

The lighting device 10A is disposed at a position away from the first inspection surface K1 in the direction of a generatrix of the first inspection surface K1 included in the outer ring 300A, namely in the direction of the central axis C of the rolling bearing 300. Specifically, the direction of the generatrix of the first inspection surface K1 included in the outer ring 300A, namely the direction of the central axis C of the rolling bearing 300, is the y direction. The lighting device 10A is disposed at a position away from the rolling bearing 300 placed on the stand 30 in the y direction. For example, as shown in FIG. 1, the lighting device 10A is disposed at a position away from (above) the rolling bearing 300 placed on the stand 30 by a distance h in the +y direction. The lighting device 10A may be disposed at a position away from (below) the rolling bearing 300 placed on the stand 30 in the −y direction.

For example, the lighting device 10A is a planar light-emitting lighting device, namely what is called a flat lighting device. Specifically, the lighting device 10 of this example surface-emits light from a light source (such as an LED), not shown. In the following description, the lighting device 10A refers to a surface that emits light, namely a light-emitting surface itself. The lighting device 10A emits light from the light source as less directional diffused light by using a diffuser, a reflector, etc., not shown. Preferably, the lighting device 10A emits white light. The difference between presence and absence of defects is clearer with white light than with red light, green light, blue light, etc. Defect detection accuracy can therefore be improved.

As shown in FIG. 1, the lighting device 10A is disposed such that at least a part of the lighting device 10A is located on the side in the +x direction (the side closer to the camera 20) of the outer ring 300A. That is, as shown in FIG. 1, an angle θ between a straight line connecting two ends e, E11 and the x direction is smaller than 90° that is the angle formed with these two ends E11, e being aligned in the y direction. The end e is an end on the side in the +x direction of the outer ring 300A, and the end E11 is an end on the side in the +x direction of the light emitting surface of the lighting device 10A. The lighting device 10A thus emits light from the light source to the first inspection surface K1 in the direction D2 different from the shooting direction D1 of the camera 20.

Preferably, the stand 30 can rotate about an axis M as shown by an arrow in FIG. 1 as controlled by, e.g., the PC 500. The rolling bearing 300 is placed on the stand 30 such that its central axis C is aligned with the axis M of the stand 30. Since the stand 30 is rotatable, the rolling bearing 300 placed on the stand 30 rotates about its central axis C, and a part of the surface of the rolling bearing 300 which faces the camera 20 changes as the rolling bearing 300 rotates. Preferably, the PC 500 controls the camera 20 to shoot at the timing based on the rotational speed of the stand 30. The PC 500 may control the camera 20 to perform continuous shooting while the table 30 is rotating. The images of the entire outer periphery of the outer ring 300A are thus input to the PC 500.

Figure 2:
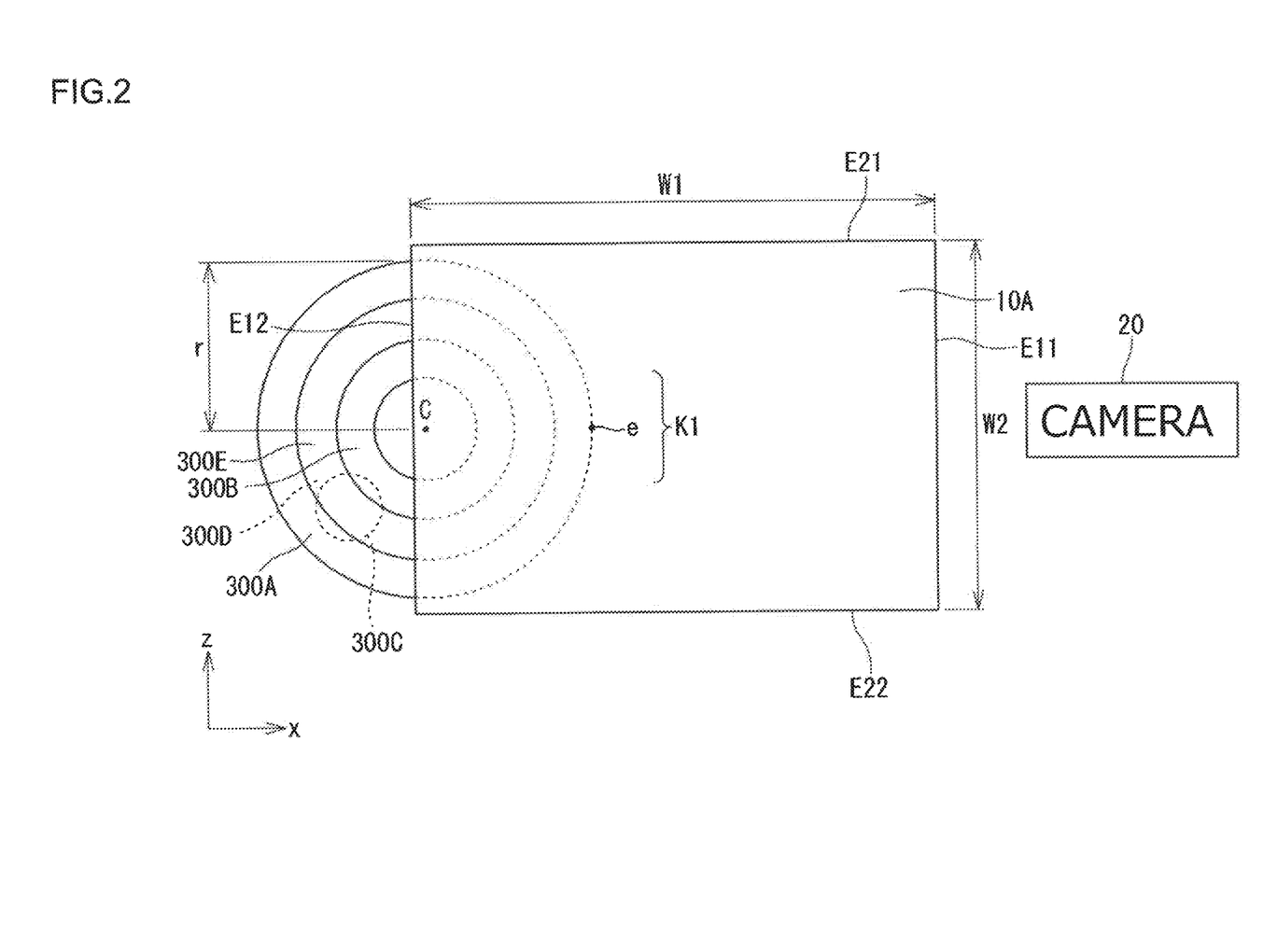
FIG. 2 is a schematic plan view showing a main part of the visual inspection device of FIG. 1.

FIG. 2 is a schematic plan view showing a main part of the visual inspection device 100 according to the first embodiment. In the plane shown in FIG. 2, the z direction is the direction perpendicular to the x direction.

Referring to FIG. 2, an end E12 on the side in the −x direction of the light emitting surface of the lighting device 10A is located on the side in the −x direction with respect to the central axis C of the rolling bearing 300 placed on the stand 30. As described above, the end E11 on the side in the +x direction of the light emitting surface is located closer to the camera 20 than the end (end on the side in the +x direction) e of the outer periphery of the outer ring 300A of the rolling bearing 300 placed on the stand 30, namely the end e located closest to the camera 20. That is, the length W1 in the x direction of the light emitting surface of the lighting device 10A is larger than r (r is the radius of the outer periphery of the outer ring 300A of the rolling bearing 300). The range in the z direction of the light emitting surface of the lighting device 10A is larger than the diameter in the z direction of the outer periphery of the outer ring 300A of the rolling bearing 300 placed on the stand 30. That is, both ends E21, E22 in the z direction of the light emitting surface of the lighting device 10A are located outside the outer periphery of the outer ring 300A of the rolling bearing 300 placed on the stand 30. The length W2 in the z direction of the light emitting surface of the lighting device 10A is thus larger than 2r.

The light emitting surface of the lighting device 10A and the outer periphery of the outer ring 300A of the rolling bearing 300 placed on the stand 30 are in the positional relationship shown in FIGS. 1 and 2. The first inspection surface K1 included in the outer peripheral surface of the semicylindrical portion of the outer ring 300A which faces the camera 20 is thus irradiated with light from a position away from the rolling bearing 300 in the +y direction, namely from above the rolling bearing 300. As described above, the camera 20 is disposed so as to face the first inspection surface K1, and the shooting range of the camera 20 includes the first inspection surface K1. That is, at least the first inspection surface K1 is irradiated with light by the lighting device 10A.

Figure 3:
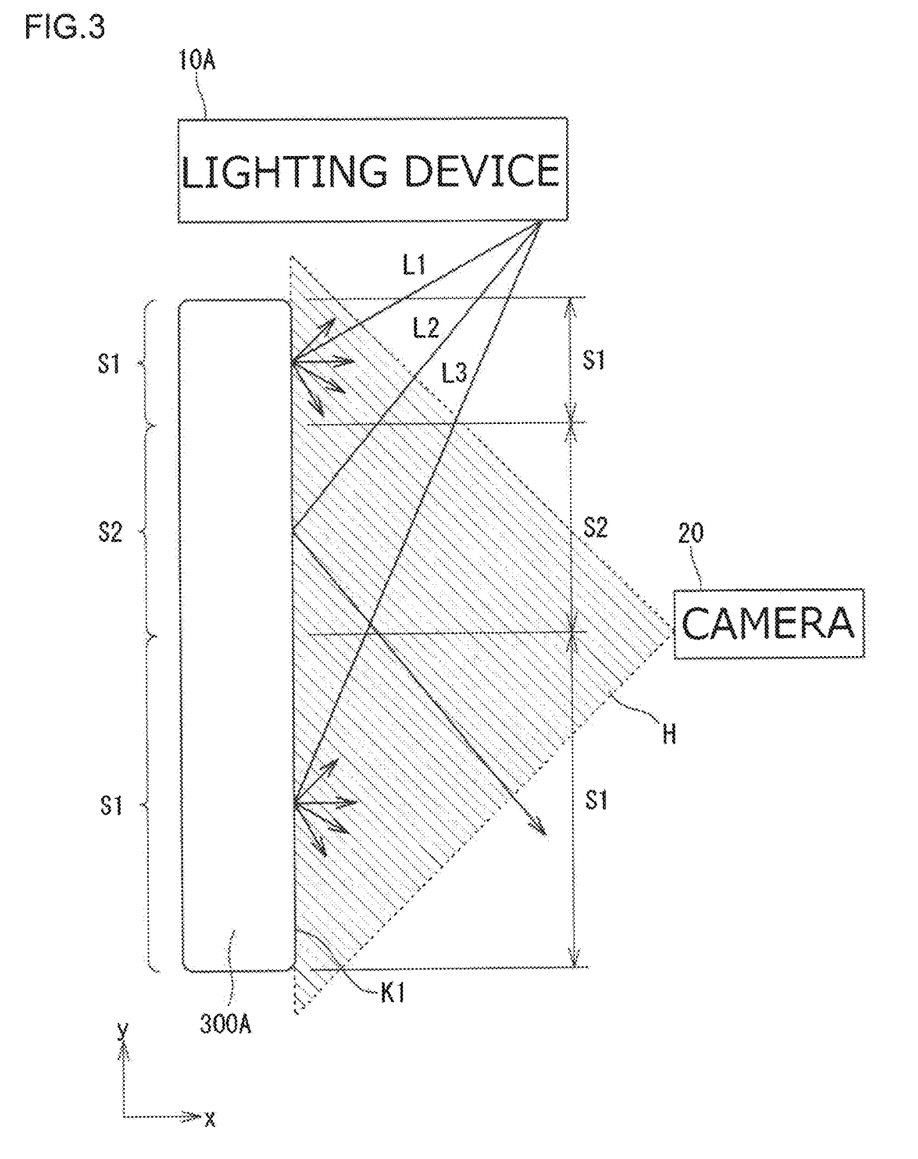
FIG. 3 is a schematic view illustrating the principles of inspection.

The principles of inspection with the visual inspection device 100 will be described with reference to FIG. 3. FIG. 3 is a schematic enlarged view of the visual inspection device 100 as viewed in the horizontal direction, showing the lighting device 10A, the camera 20, and a portion near the outer periphery of the outer ring 300A of the rolling bearing 300 placed on the stand 30. The outer periphery of the outer ring 300A shown in FIG. 3 corresponds to the first inspection surface K1. Reference character H in FIG. 3 represents the field-of-view range of the camera 20, namely the shooting range of the camera 20.

The visual inspection device 100 emits light (preferably white light) from the lighting device 10A to the first inspection surface K1 included in the outer periphery of the outer ring 300A, and checks if there are any irregularities on the first inspection surface K1 based on the amount of light reflected from the first inspection surface K1 into the camera 20. For example, irregularities on the first inspection surface K1 are hollows called shoe marks that are formed by an object such as abrasive powder contacting the surface mainly during surface grinding in a manufacturing process, and hollows such as flaws (scratches, dents, etc.) that are formed by an object contacting the surface after manufacturing. In the following description, irregularities on the first inspection surface K1 are shoe marks.

An industrial product having a glossy surface by grinding or coating has high surface reflectance. Since the outer peripheral surface of the rolling bearing 300 is ground, the outer peripheral surface of the rolling bearing 300 has high reflectance. In the case where the first inspection surface K1 has a region having irregularities and a region having no irregularities, the amount of light reflected from the region having irregularities is different from the amount of light reflected from the region having no irregularities. Specifically, referring to FIG. 3, it is herein assumed that the range of the first inspection surface K1 which is included in the field-of-view range H of the camera 20 includes a region S2 having shoe marks and regions S1 having no shoe marks. The region S2 is ground with an object such as abrasive powder being pressed against the surface. The region S2 therefore has lower surface roughness than the regions S1. Accordingly, as shown in FIG. 3, the amount by which light L2 emitted to the region S2 is specularly reflected by the region S2 is larger than the amount by which light L1 emitted to the region S1 is diffusely reflected by the region S1 due to its surface roughness.

As shown in FIGS. 1 and 2, the light L2 is emitted to the region S2 in the direction D2 different from the shooting direction D1 of the camera 20. Accordingly, as shown in FIG. 3, the component of the light L2 specularly reflected from the region S2 goes out of the field-of-view range H of the camera 20. The amount of component of the emitted light L1 which is specularly reflected from the region S1 is smaller than the amount of component of the emitted light L2 which is specularly reflected from the region S2. In other words, it is more likely that the component diffusely reflected from the region S1 goes into the field-of-view range H of the camera 20 than the component diffusely reflected from the region S2 goes into the field-of-view range H. That is, the amount of light reflected from the region S1 into the field-of-view range H of the camera 20 is larger than the amount of light reflected from the region S2 into the field-of-view range H of the camera 20. Accordingly, an image of the first inspection surface K1 shot with the camera 20 has a difference in shade between the regions S1, S2. That is, in the image, the region S1 is lighter (have a higher lightness value) than the region S2. In other words, a dark part in the image corresponds to a shoe mark.

Figure 4:
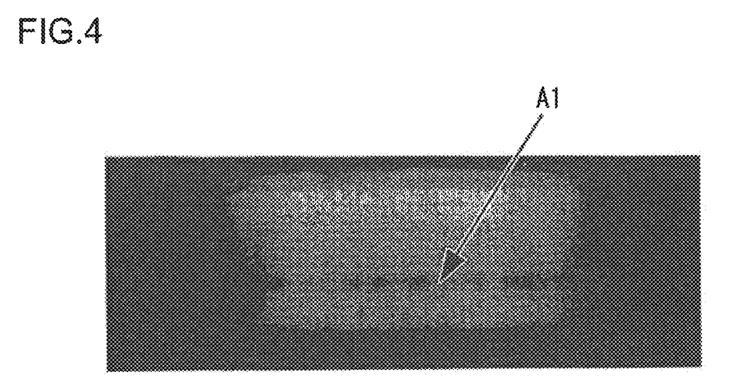
FIG. 4 shows a captured image of a first inspection surface obtained by the visual inspection device of the embodiment.

FIG. 4 shows an image of the first inspection surface K1 shot with the camera 20 of the visual inspection device 100. Referring to FIG. 4, black lines in an area A1 represent shoe marks on the first inspection surface K1. As shown in FIG. 4, in the visual inspection device 100, the image of the first inspection surface K1 has a distinct difference in shade between the region having irregularities such as shoe marks and the region having no irregularities.

For example, the CPU 50 of the PC 500 performs an analysis process to analyze the shades, i.e., lightness, of the image (FIG. 4) captured by the camera 20. The CPU 50 can thus detect the region S2 included in the first inspection surface K1, namely the presence of shoe marks. The captured image may be displayed on a display, not shown, of the PC 500 and the presence of shoe marks may be visually detected by the user.

Figure 5:
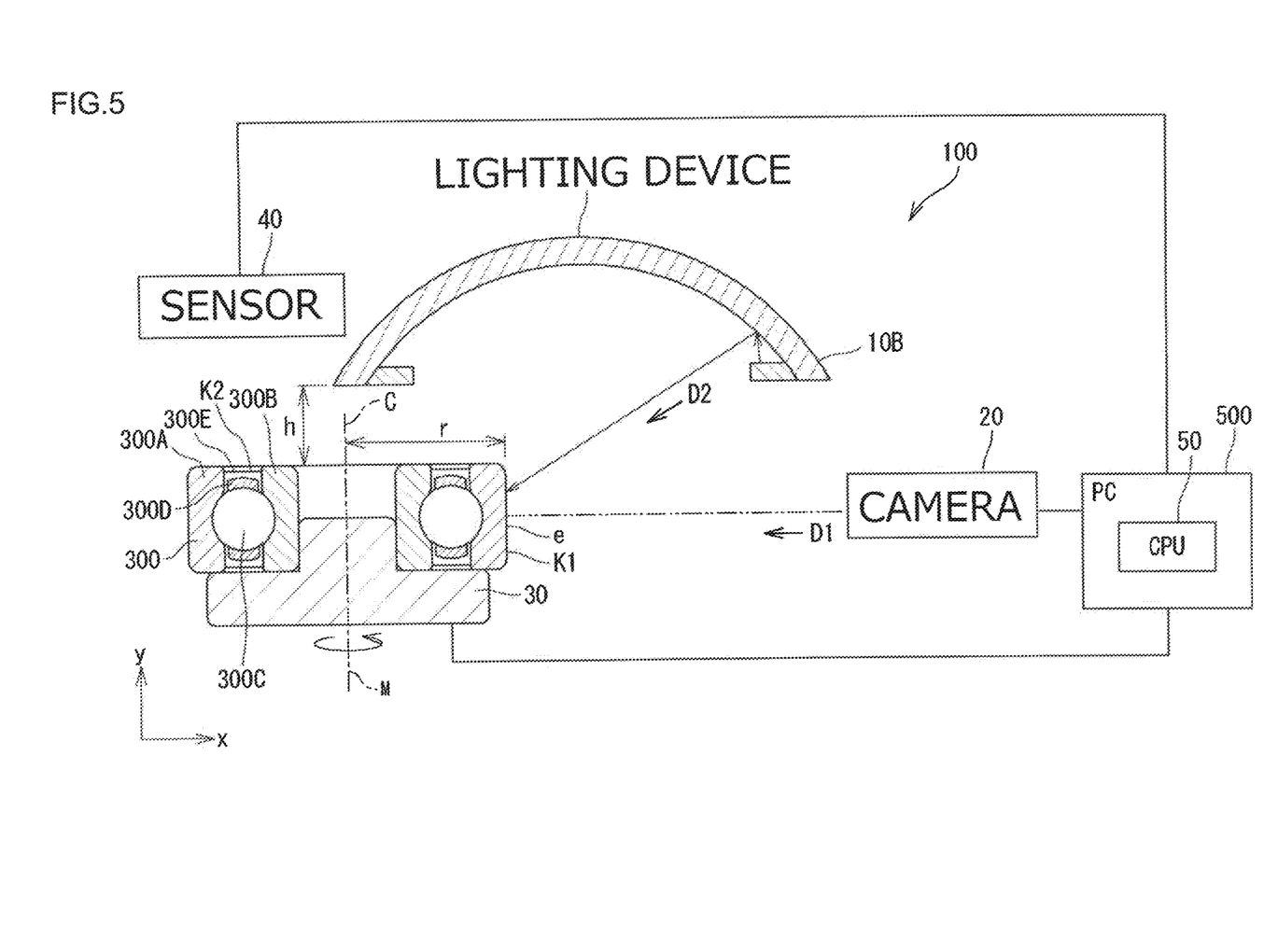
FIG. 5 is a schematic view showing another example of a lighting device.

In the above example, the lighting device 10A included in the visual inspection device 100 is a surface light-emitting lighting device called a flat lighting device. However, the lighting device included in the visual inspection device 100 is not limited to the flat lighting device as long as the lighting device emits light from a light source as diffused light. FIG. 5 is a view showing another example of the lighting device. Referring to FIG. 5, for example, the visual inspection device 100 may include a lighting device 10B having a dome-shaped (curved) reflector above a light source. The lighting device 10B reflects emitted light from the light source in various directions by the curved reflector to diffuse the emitted light. The lighting device 10B thus emits the diffused light to the rolling bearing 300.

Figure 6:
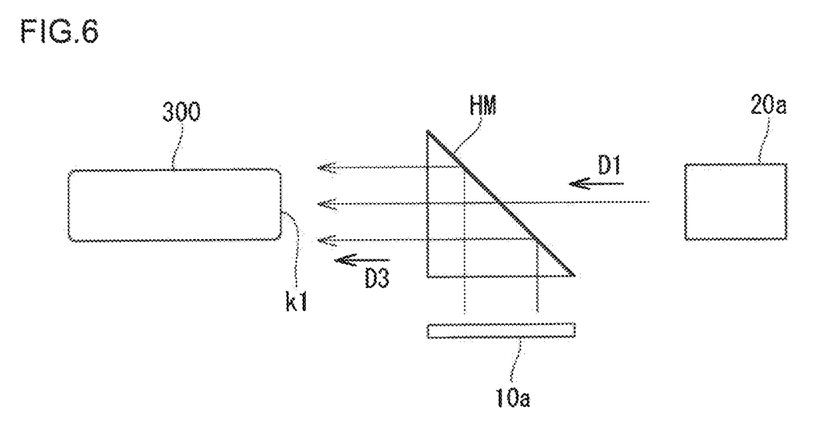
FIG. 6 is a schematic view showing a conventional inspection device.
Figure 7:
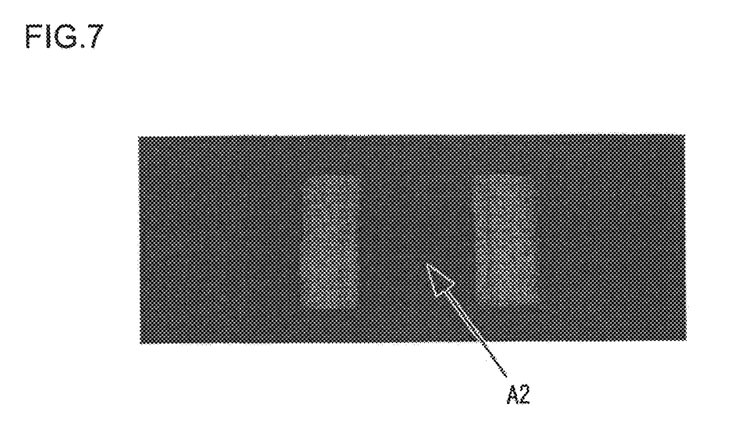
FIG. 7 shows a captured image of a first inspection surface obtained by the conventional inspection device.

Effects of visual inspection by the visual inspection device 100 according to the present embodiment will be examined in comparison with inspection results obtained by a conventional inspection device. FIG. 6 is a schematic view of the configuration of a conventional inspection device used for comparison. FIG. 7 is a captured image obtained as an inspection result. The object of the image of FIG. 7 is the same rolling bearing as that in the image of FIG. 4. In the image of FIG. 7, the same surface of the rolling bearing was shot as the first inspection surface K1.

Referring to FIG. 6, the conventional inspection device uses a lighting device 10a that emits light that is more directional than diffused light. Accordingly, the direction D3 in which the lighting device 10a emits light to the rolling bearing 300 is aligned with the shooting direction D1 of a camera 20a. For example, as shown in FIG. 6, the direction D3 may be aligned with the direction D1 by using a half mirror HM.

An area A2 in FIG. 7 corresponds to the area A1 in FIG. 4. Black lines corresponding to shoe marks can be seen in the area A1 in FIG. 4. In the captured image of FIG. 7, however, the entire area near the middle part of the image is dark and no black lines corresponding to shoe marks can be seen in the area A2. As can also be seen from FIG. 7, the image obtained by the conventional inspection device is not uniform in lightness. The reason for this is as follows. As shown in FIG. 6, light that is more directional than diffused light is emitted in the same direction D3 as the shooting direction D of the camera 20a. Accordingly, the proportion of the amount of light reflected from the first inspection surface K1 into the camera 20a to the amount of light emitted from the lighting device 10a is higher as compared to the visual inspection device 100 in which the direction D2 in which the lighting device 10A (or the lighting device 10B) emits light is different from the shooting direction D of the camera 20. Another reason is that most of light emitted from the lighting device 10a passes through the field-of-view range (corresponding to the range H in FIG. 3) of the camera 20a and is captured in the image. In the inspection with the conventional inspection device as well, the amount of light reflected from the first inspection surface K1 varies between the region having shoe marks and the region having no shoe marks due to the difference in reflectance between these regions. However, since the overall amount of light entering the camera 20a is large, the difference in shade between these regions is small in the image captured by the camera 20a.

Direct light that is emitted from the lighting device 10a is more directional than diffused light and is emitted in the same direction D3 as the shooting direction D1 of the camera 20a. Accordingly, in the case where the first inspection surface K1 is a curved surface as in the rolling bearing 300, light emitted from the lighting device 10a is mainly incident on a part of the first inspection surface K1 which is located directly in front of the camera 20a, and the amount of light that is incident on the first inspection surface K1 decreases with the distance from the part located directly in front of the camera 20a. As can also be seen from FIG. 7, the shooting range is therefore smaller than that in FIG. 4.

In the visual inspection device 100 according to the present embodiment, the lighting device 10A (or the lighting device 10B) is disposed at the position shown in FIGS. 1 and 2 and emits less directional diffused light. The direction D2 in which the lighting device 10A (or the lighting device 10B) emits light can thus be made different from the shooting direction D1 of the camera 20. The difference between the amount of light reflected into the camera 20 from the region of the first inspection surface K1 having shoe marks and the amount of light reflected into the camera 20 from the region of the first inspection surface K1 having no shoe marks can therefore be increased. Accordingly, the image (FIG. 4) obtained by the visual inspection device 100 has a larger difference in shade between the region having shoe marks and the region having no shoe marks, as compared to the image (FIG. 7) obtained by the conventional inspection device. This can improve the accuracy of detection of the presence of irregularities such as shoe marks on the first inspection surface K1, namely the accuracy of detection of irregularities such as flaws on the surface which are detected as defective gloss. Since the image obtained by the visual inspection device 100 has a larger difference in shade between the region having shoe marks and the region having no shoe marks, the presence of irregularities such as shoe marks on the first inspection surface K1 can be automatically detected with high accuracy by a method such as the CPU 50 of the PC 500 performing an image analysis process to make a comparison with a threshold.

Since the lighting device 10A (or the lighting device 10B) emits less directional diffused light, the range of the outer peripheral surface of the outer ring 300A which is irradiated with light can be increased. Light is thus uniformly emitted to at least the entire first inspection surface K1 and an image with a distinct difference in shade is obtained. This can improve the accuracy of detection of the presence of irregularities such as shoe marks on the first inspection surface K1, namely accuracy of detection of irregularities such as flaws on the surface which are detected as defective gloss.

The visual inspection device 100 according to the second embodiment further includes the sensor 40 as shown in FIG. 1. The sensor 40 is a displacement sensor. The sensor 40 uses laser light etc. to contactlessly measure the distance to a sealing device disposed at an end face of the rolling bearing 300 placed on the stand 30. One example of the sealing device is the bearing seal 300E disposed at the end face of the rolling bearing 300 as shown in FIG. 1. Another example of the sealing device is a shield plate. The sensor 40 measures the distance to a second inspection surface K2. The second inspection surface K2 is the surface included in the end face of the rolling bearing 300 at which the bearing seal 300E is disposed. The sensor 40 is disposed so as to be located away from (e.g., above) the bearing seal 300E of the rolling bearing 300 placed on the stand 30 in the y direction and so as to be located farther away from the camera 20 than the side of the outer ring 300A which faces the camera 20. Preferably, the sensor 40 is disposed on the opposite side of the lighting device 10A (or the lighting device 10B) from the camera 20 on the plane including the camera 20 and the central axis C of the rolling bearing 300.

In the visual inspection device 100, the stand 30 rotates about its axis M and the first inspection surface K1 is shot with the camera 20 while the stand 30 is rotating. In this case, since the sensor 40 is disposed as described above, the distance to the second inspection surface K2 can be simultaneously measured with the sensor 40. That is, in the visual inspection device 100 according to the second embodiment, the first inspection surface K1 included in the outer peripheral surface of the outer ring 300A is shot with the camera 20, and at the same time, the distance to the second inspection surface K2 included in the surface at which the bearing seal 300E is disposed is measured with the sensor 40. In the visual inspection device 100 according to the second embodiment, shooting of the first inspection surface K1 and measurement of the distance to the second inspection surface K2 can be performed by a single detection operation.

Whether irregularities are present on the first inspection surface K1 or not is detected by analyzing the image in a manner described above. Inspection of the first inspection surface K1 can thus be conducted. The PC 500 receives the distance measured by the sensor 40 during the same inspection operation, and performs analysis such as comparing the received distance to the second inspection surface K2 with an appropriate distance stored in advance. The visual inspection device 100 thus detects defective fitting of the sealing device such as the bearing seal 300E in the visual inspection. Accordingly, the visual inspection device 100 can inspect for defective fitting of the sealing device.

In the visual inspection device 100 according to the second embodiment, inspection time can be reduced as compared to the case where the above two inspections are performed by different inspection operations. Moreover, the inspection device can be reduced in size as compared to the case where inspection devices are separately prepared for the two inspections.

The embodiments disclosed above are by way of example in all respects and should not be construed as restrictive. The scope of the present invention is defined by the claims rather than by the above description and is intended to cover all the modifications and variations that are made without departing from the spirit and scope of the claims.

The present invention can improve visual inspection accuracy.

What is claimed is:

1. A visual inspection device for inspecting an bearing, the visual inspection device comprising:
a camera having a central axis that is disposed so as to face in a direction perpendicular to a first inspection surface of a rolling bearing to be inspected, the camera being configured to capture an image of the first inspection surface, the rolling bearing including an inner ring and an outer ring, the first inspection surface being included in an outer peripheral surface of the outer ring;
a lighting device that emits light from a light source as diffused light to the first inspection surface, the light being emitted in a direction different from the direction in which the camera captures the image of the first inspection surface, and a central axis of the lighting device is offset from the central axis of the camera; and a displacement sensor that measures a distance to a second inspection surface of the rolling bearing, the displacement sensor being disposed at a position farther away from the camera than a side of the outer ring which faces the camera.

2. The visual inspection device according to claim 1, further comprising:

a stand on which the rolling bearing is placed such that the first inspection surface included in the outer peripheral surface of the rolling bearing faces the camera, and the direction perpendicular to the direction in which the camera captures the image of the first inspection surface is aligned with a direction of a central axis of the rolling bearing, the outer peripheral surface of the rolling bearing being a circumferential surface, wherein the lighting device is disposed at a position away from the rolling bearing placed on the stand in the direction of the central axis of the rolling bearing.

3. A visual inspection device for inspecting a rolling bearing, the visual inspection device comprising:

a camera that is disposed so as to face in a direction perpendicular to a first inspection surface of the rolling bearing to be inspected, the rolling bearing including an inner ring and an outer ring, the camera being configured to capture an image of the first inspection surface, and the first inspection surface being included in an outer peripheral surface of the outer ring of the rolling bearing;

a lighting device that emits light from a light source as diffused light to the first inspection surface, the light being emitted in a direction different from a direction in which the camera captures the image of the first inspection surface; and a displacement sensor that measures a distance to a second inspection surface of the rolling bearing, the displacement sensor being disposed at a position farther away from the camera than a side of the outer ring which faces the camera.

4. The visual inspection device according to claim 3, further comprising:

a stand on which the rolling bearing is placed such that the first inspection surface included in the outer peripheral surface of the rolling bearing faces the camera, and the direction perpendicular to the direction in which the camera captures the image of the first inspection surface is aligned with a direction of a central axis of the rolling bearing, the outer peripheral surface of the rolling bearing being a circumferential surface, wherein the lighting device is disposed at a position away from the rolling bearing placed on the stand in the direction of the central axis of the rolling bearing.

5. A method for visually inspecting a rolling bearing by using an image obtained by capturing an image of a first inspection surface of the rolling bearing with a camera having a central axis disposed so as to face in a direction perpendicular to the first inspection surface, the rolling bearing including an inner ring and an outer ring, and the first inspection surface is included in an outer peripheral surface of the outer ring, the method comprising:

emitting light from a light source as diffused light to the first inspection surface by a lighting device in a direction different from the direction in which the camera captures the image of the first inspection surface, the lighting device having a central axis that is offset from the central axis of the camera;

measuring, using a displacement sensor, a distance to a second inspection surface of the rolling bearing, the displacement sensor being disposed at a position farther away from the camera than a side of the outer ring which faces the camera; and capturing the image of the first inspection surface irradiated with the diffused light by the camera.

* * * * *